(12) United States Patent
D'Alfonso et al.

(10) Patent No.: US 11,332,299 B2
(45) Date of Patent: May 17, 2022

(54) PACKAGE FOR COMPONENTS OF AEROSOL GENERATING DEVICES

(71) Applicant: G.D SOCIETA' PER AZIONI, Bologna (IT)

(72) Inventors: Lorena D'Alfonso, Lettomappello (IT); Roberto Polloni, Modigliana (IT); Luca Federici, Bologna (IT)

(73) Assignee: G.D SOCIETA' PER AZIONI, Bologna (IT)

( * ) Notice: Subject to any disclaimer, the term of this patent is extended or adjusted under 35 U.S.C. 154(b) by 0 days.

(21) Appl. No.: 16/754,391

(22) PCT Filed: Oct. 11, 2018

(86) PCT No.: PCT/IB2018/057897
§ 371 (c)(1),
(2) Date: Apr. 8, 2020

(87) PCT Pub. No.: WO2019/073438
PCT Pub. Date: Apr. 18, 2019

(65) Prior Publication Data
US 2020/0317426 A1      Oct. 8, 2020

(30) Foreign Application Priority Data

Oct. 11, 2017  (IT) .......................... 102017000114214

(51) Int. Cl.
*B65D 83/04*    (2006.01)
*B65D 75/36*    (2006.01)

(52) U.S. Cl.
CPC ....... *B65D 83/0463* (2013.01); *B65D 75/367* (2013.01)

(58) Field of Classification Search
CPC .......................... B65D 75/367; B65D 83/0463
(Continued)

(56) References Cited

U.S. PATENT DOCUMENTS

| 4,262,837 A | * | 4/1981 | Fremion | ................... B65D 5/32 229/117.16 |
| 6,907,880 B1 | | 6/2005 | Heckenmuller et al. | |

(Continued)

OTHER PUBLICATIONS

International Application No. PCT/IB2018/057897, International Search Report and Written Opinion, dated Mar. 5, 2019.

*Primary Examiner* — Luan K Bui
(74) *Attorney, Agent, or Firm* — Marshall, Gerstein & Borun LLP

(57) ABSTRACT

Package for components of aerosol generating devices, comprising: at least two components; a sleeve comprising a first wall and a second wall opposite and parallel to each other, and a first opening and a second opening opposite to each other; a first and a second blister pack containing the components and slidable relative to the sleeve through the first opening and the second opening, respectively; a first guide flap extending from the second wall of the sleeve at the second opening to create a first slot with the second wall; a second guide flap extending from the first wall of the sleeve at the first opening to create a second slot with the first wall; a first sliding flap integral with the first blister pack and a second sliding flap integral with the second blister pack which are arranged in the first slot and in the second slot, respectively, and that are shaped to slide in the first slot and in the second slot, respectively.

11 Claims, 11 Drawing Sheets

(58) Field of Classification Search
USPC .................................. 206/461, 468, 531, 800
See application file for complete search history.

(56) References Cited

U.S. PATENT DOCUMENTS

| | | | |
|---|---|---|---|
| 2006/0102512 A1* | 5/2006 | Lo Duca ............ | B65D 83/0463 |
| | | | 206/531 |
| 2008/0053863 A1* | 3/2008 | Glydon .................. | B65D 85/60 |
| | | | 206/531 |
| 2008/0272021 A1* | 11/2008 | Cavazza .............. | B65D 5/4229 |
| | | | 206/528 |
| 2009/0250056 A1 | 10/2009 | Pentafragas | |
| 2010/0116693 A1 | 5/2010 | Hession | |
| 2010/0230316 A1* | 9/2010 | Wharton ................ | B65D 5/728 |
| | | | 206/462 |
| 2010/0243509 A1 | 9/2010 | Gelardi | |
| 2015/0041339 A1 | 2/2015 | Jones et al. | |
| 2017/0210531 A1* | 7/2017 | Parker ..................... | A61J 1/035 |

* cited by examiner

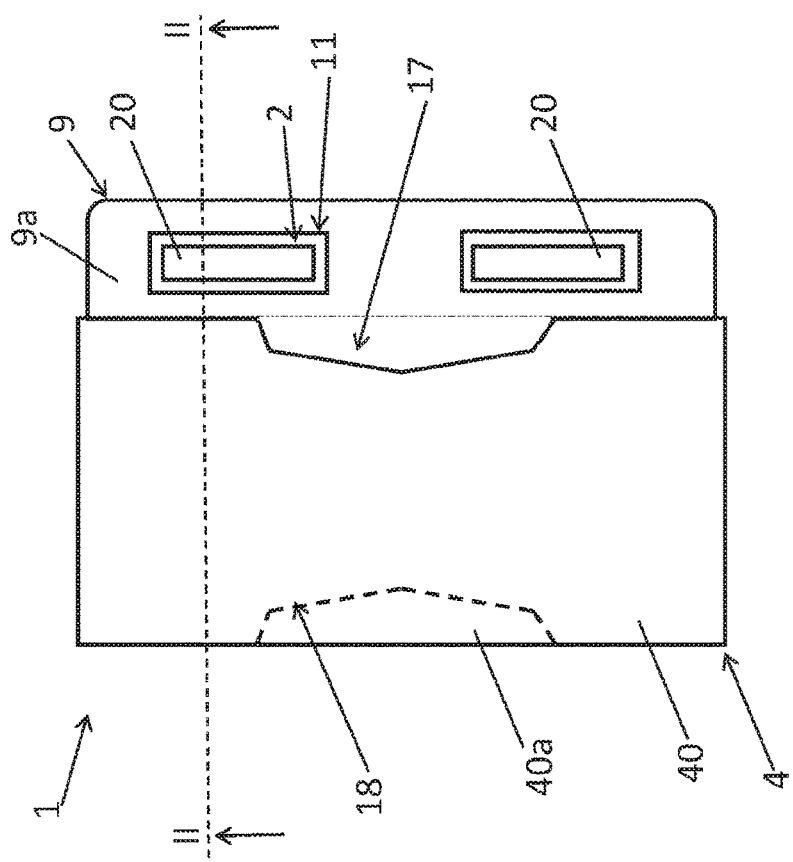
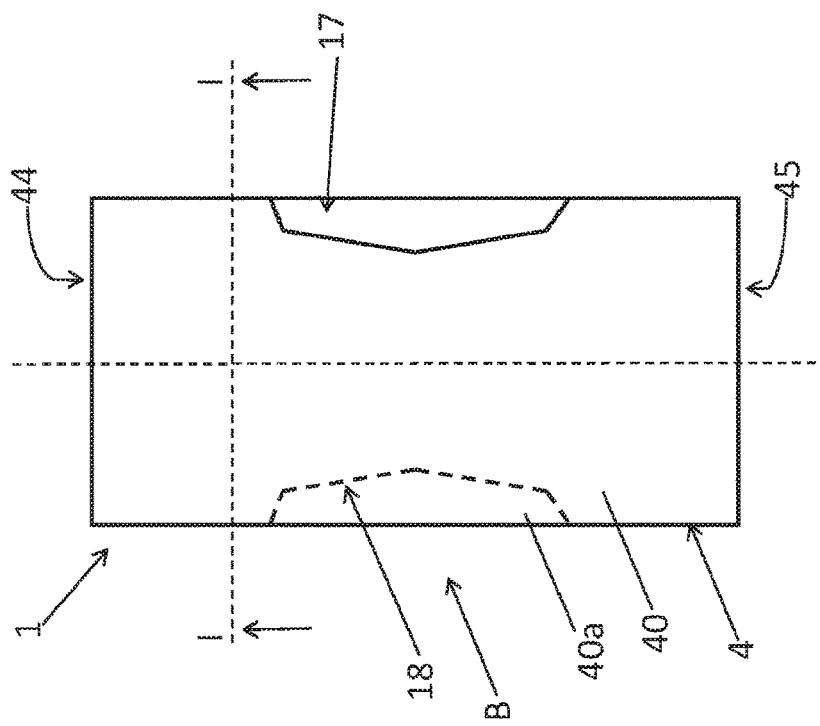

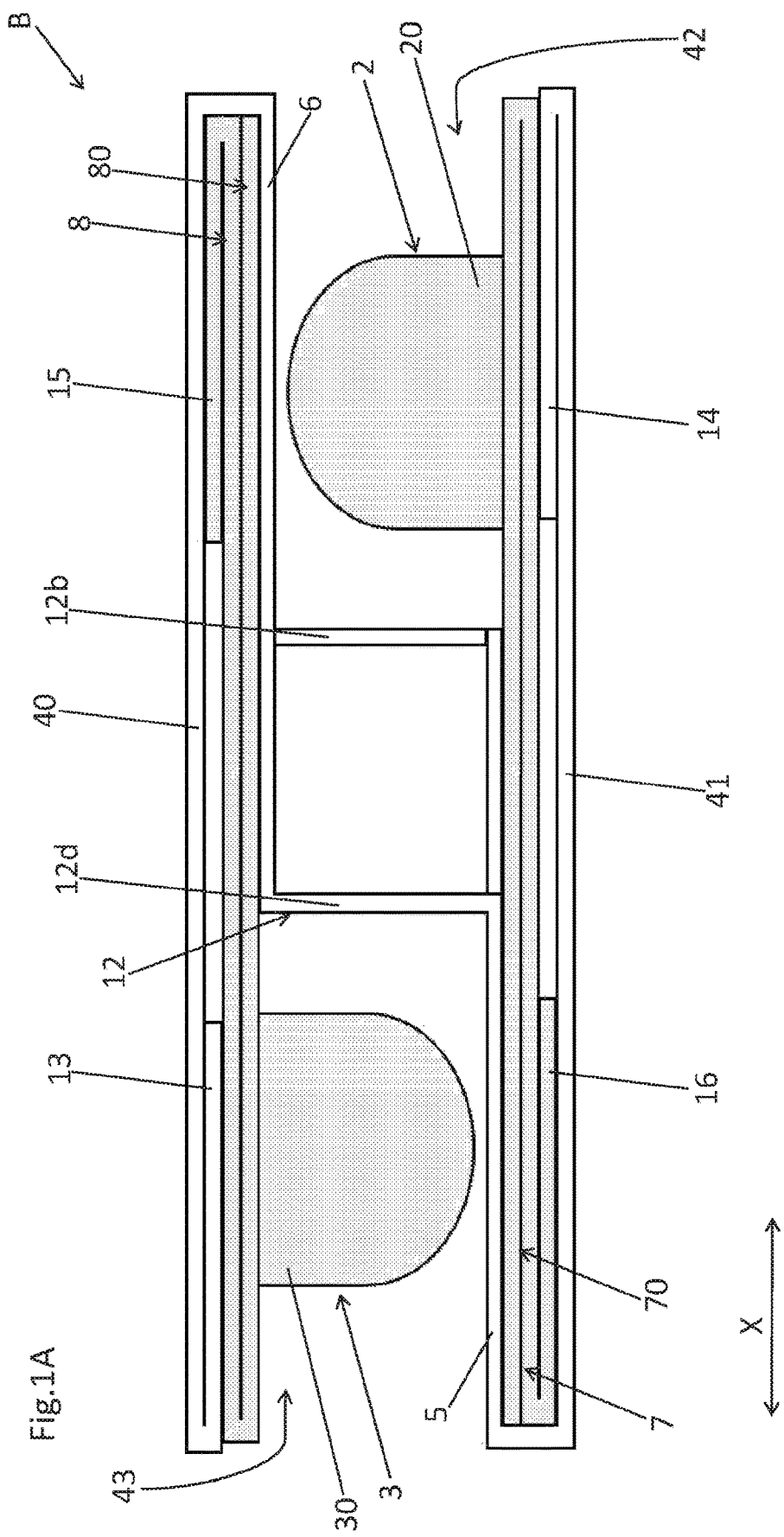

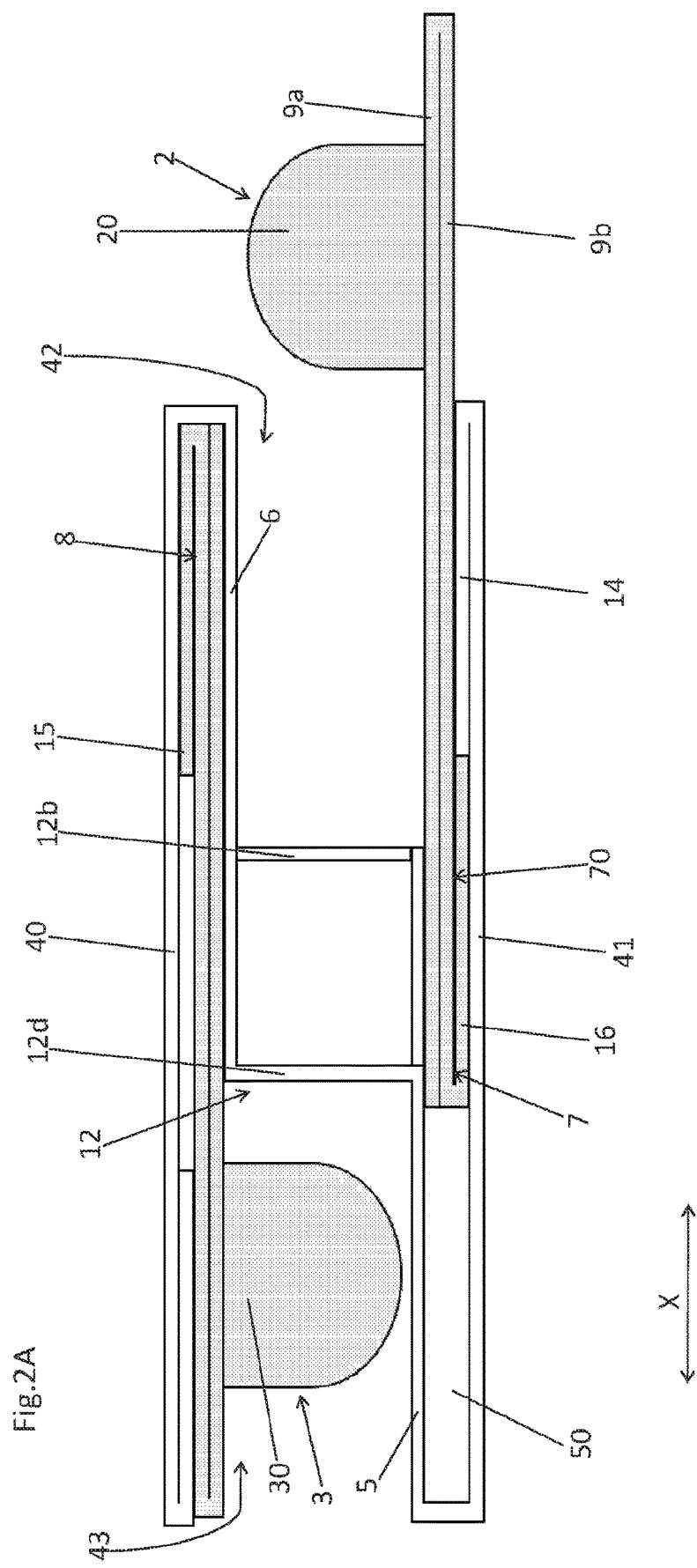

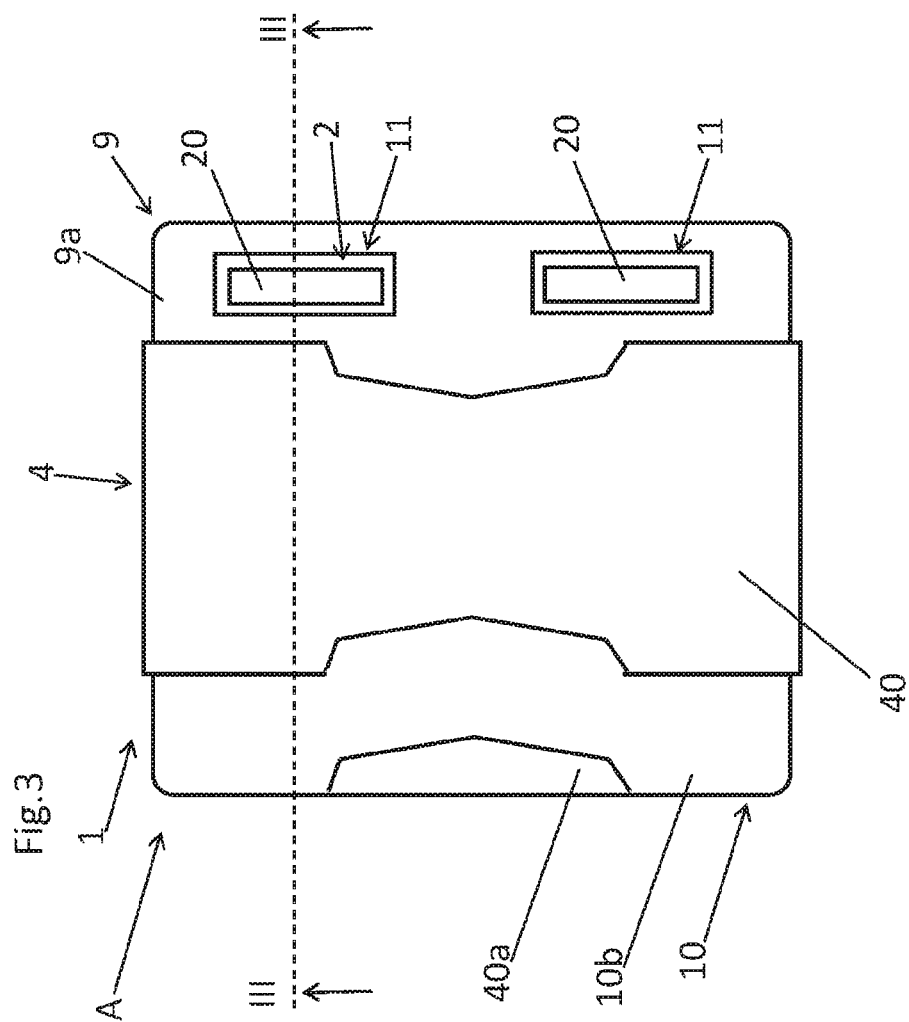

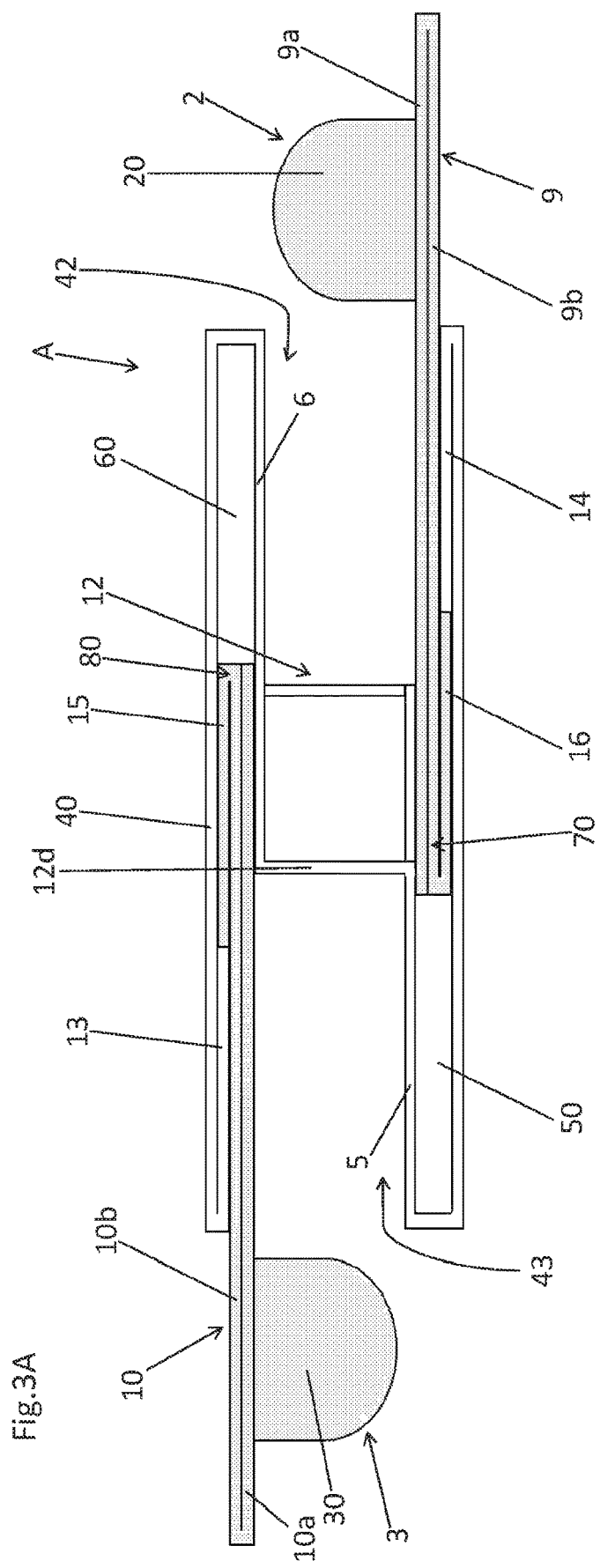

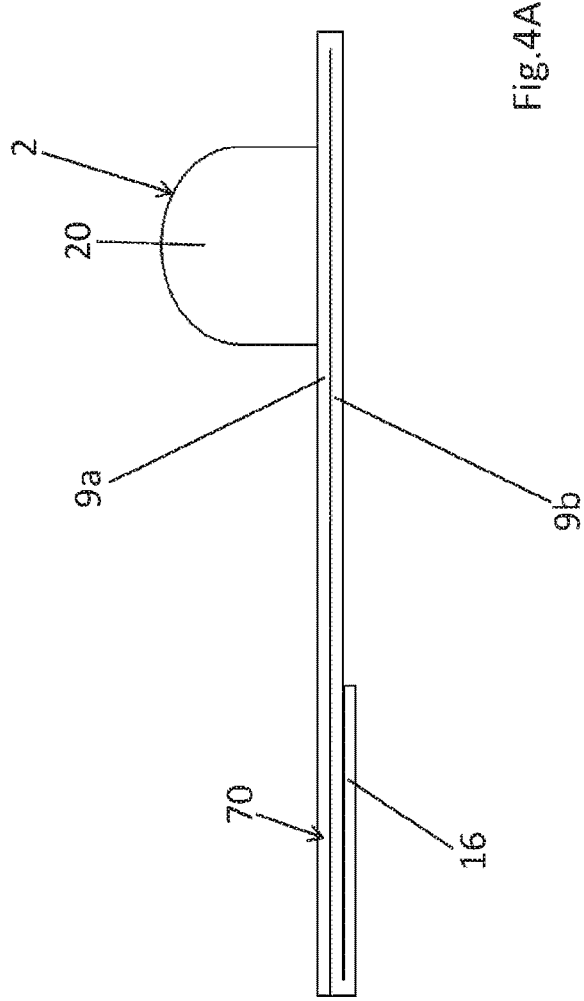
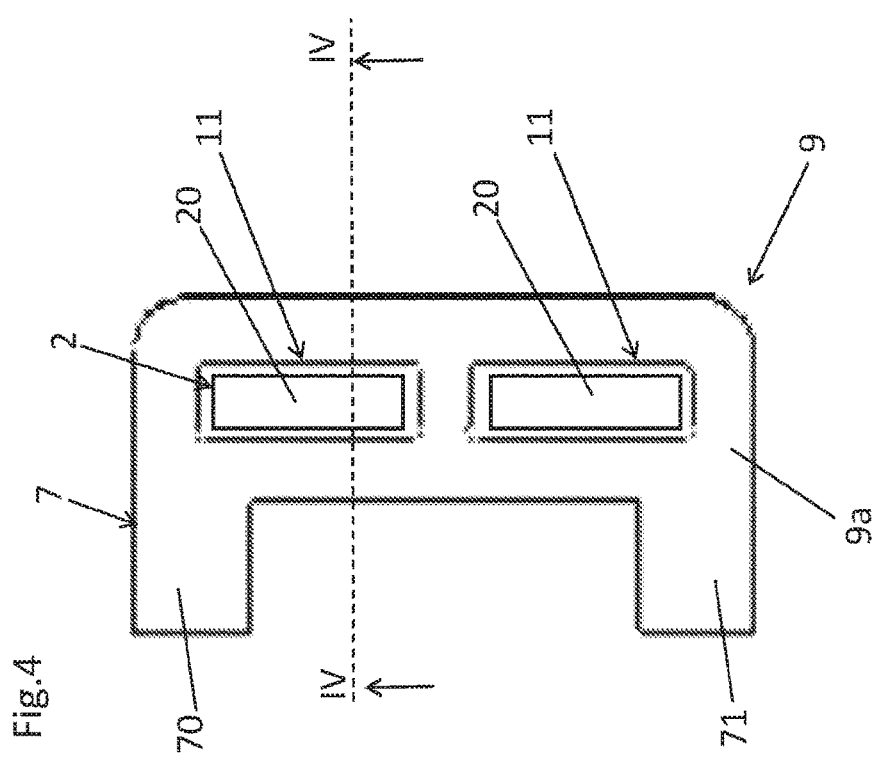

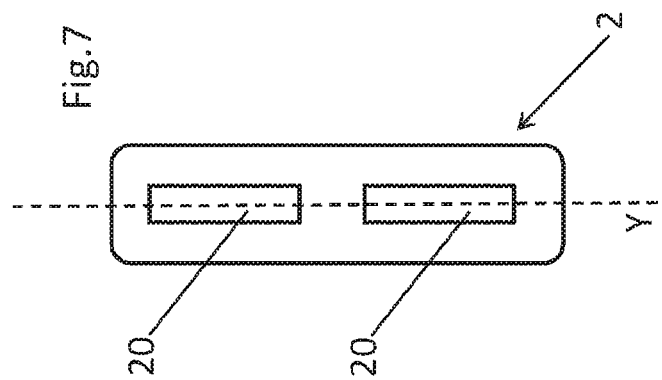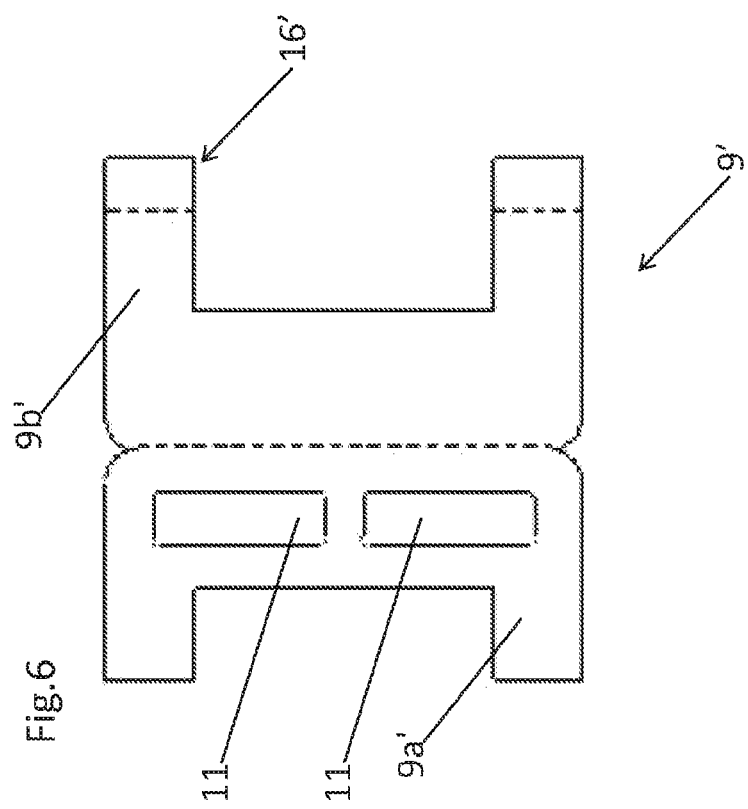

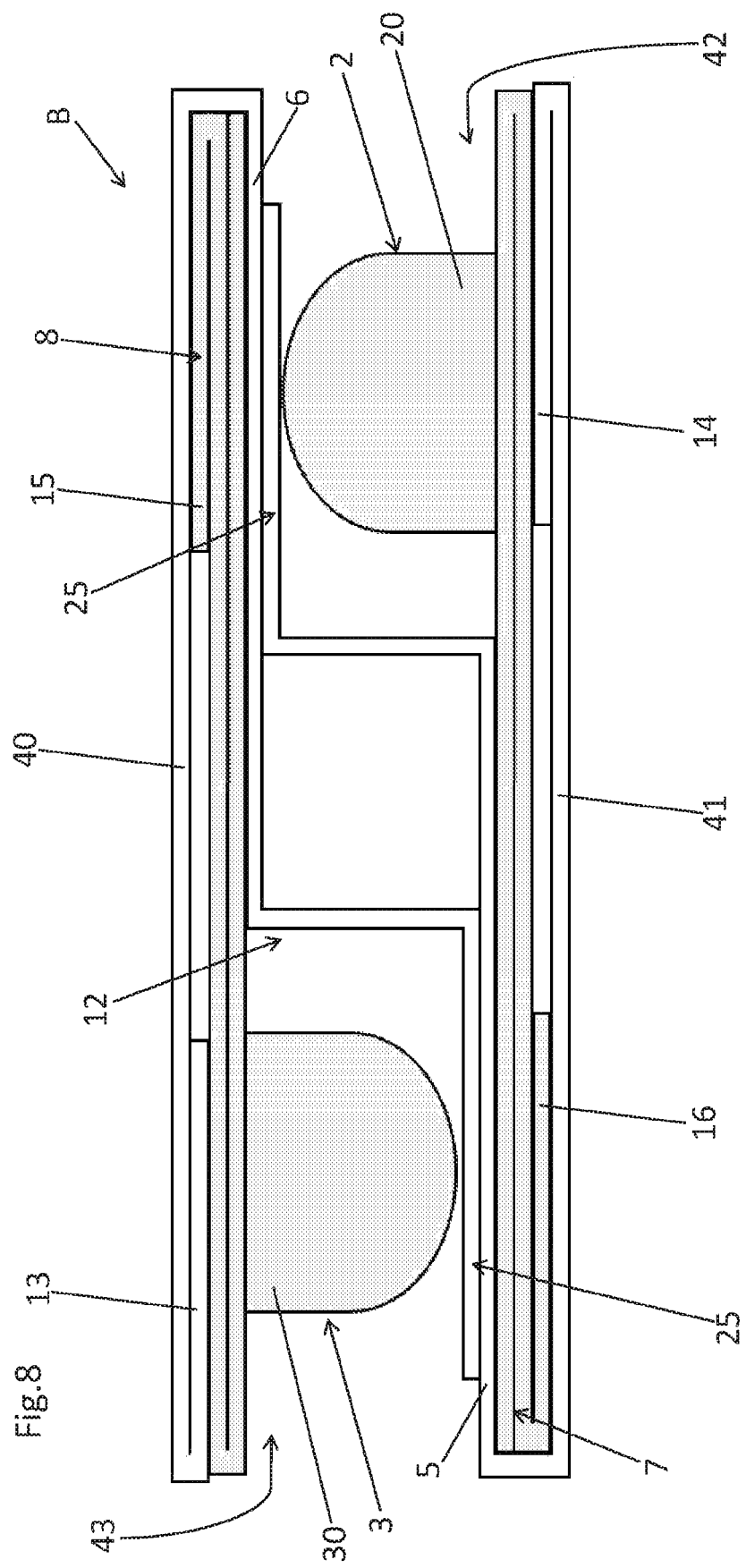

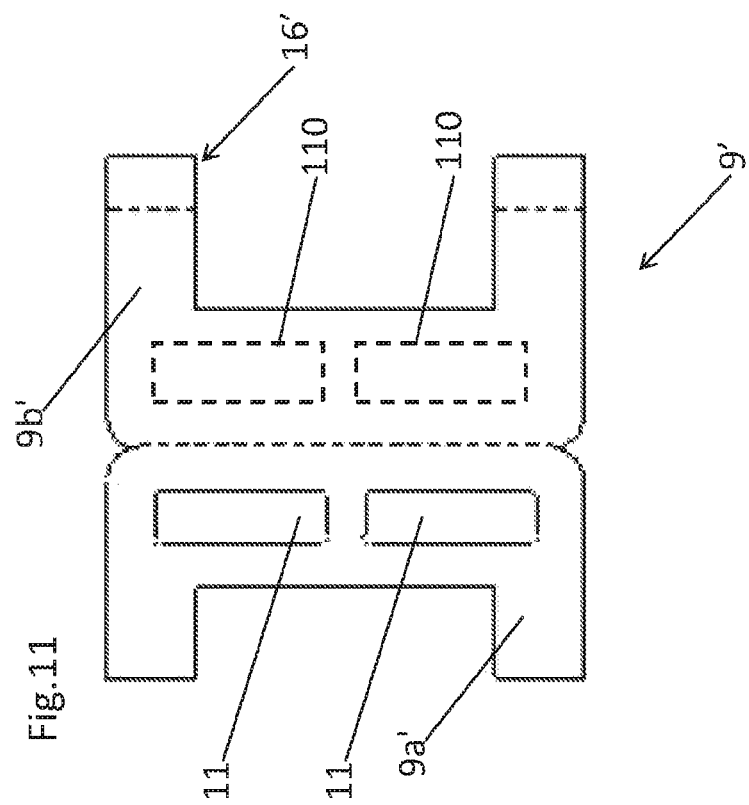
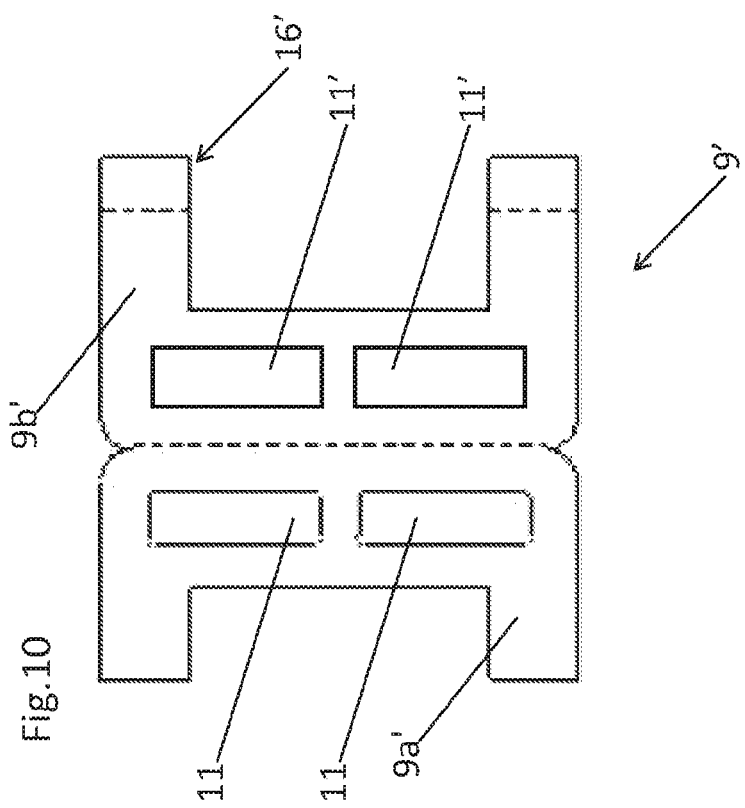

US 11,332,299 B2

PACKAGE FOR COMPONENTS OF AEROSOL GENERATING DEVICES

CROSS-REFERENCE TO RELATED APPLICATIONS

This is the U.S. national phase of International Application No. PCT/IB2018/057897, filed Oct. 11, 2018, which claims the benefit of Italian Patent Application No. 102017000114214, filed Oct. 11, 2017.

TECHNICAL FIELD

The present invention relates to a package for components of aerosol generating devices. In particular, the present invention relates to a package in which the components are contained inside blister packs.

PRIOR ART

An aerosol generating device generally comprises, a battery, an atomizer which is powered by the battery and a cartridge containing an aromatised liquid or, possibly, a powdered material.

With particular reference to the cartridges for aerosol generating devices, in order to better preserve the contents, they are arranged, after the assembly thereof, inside blister packs.

In this regard, a package is known, comprising: two components (in particular, two cartridges); a blister pack containing the two components; an external container that contains, on the inside, the blister pack. In order to access the components, the smoker must open the external container, extract the blister pack and remove the component.

Therefore, the proposed package does not allow immediate access to the components.

The patent application US2015041339A1 describes a package for two blister packs and comprising two parallelepiped tubular shaped sleeves which are formed by folding a blank and that house the respective blister packs, in a sliding manner; each sleeve has an outer wall, an inner wall and a reinforcing wall which is connected (glued) to the inner face of the outer wall.

The patent application US2010116693A1 describes a package for two blister packs and comprising two parallelepiped tubular shaped sleeves which are formed by folding a blank and that house the respective blister packs, in a sliding manner.

DESCRIPTION OF THE INVENTION

The aim of the present invention is to overcome the aforesaid drawback.

Furthermore, it is an aim of the present invention to provide a package which, in addition to allowing immediate access to the components, allows to optimize the number of components that can contain in relation to the quantity of material used.

The aforesaid aims have been obtained by means of a package according to the appended claims.

The proposed package, due to the sliding of the two blister packs in respect to the outer sleeve, allows the smoker to access the components contained in the blister packs simply by extracting the blister pack from the sleeve. Furthermore, the proposed package, by comprising two blister packs and a single sleeve, allows to optimize the number of components that it can contain in relation to the quantity of material used.

BRIEF DESCRIPTION OF THE DRAWINGS

The present invention will now be described with reference to the attached drawings, which illustrate non-limiting embodiments, wherein:

FIG. 1 is a plan view of a first embodiment of the package object of the present invention, in which the blister packs are in the closing configuration;

FIGS. 2 and 3 are views of the package of FIG. 1, in which one or both blister packs are in the extraction configuration;

FIGS. 1A-3A are section views of FIGS. 1-3, along the sections I-I, II-II and respectively;

FIG. 4 is a plan view of the first support element of the first blister pack of the package of FIG. 1;

FIG. 4A is a section view of FIG. 4, along section IV-IV;

FIG. 6 is a view of the blank for obtaining the support element of FIG. 4;

FIG. 7 is a plan view of the first blister pack;

FIG. 8 is a cross-section view of a further embodiment of the package object of the present invention;

FIGS. 10 and 11 are respective alternative blanks to that of FIG. 6.

PREFERRED EMBODIMENTS OF THE INVENTION

Figure 5:
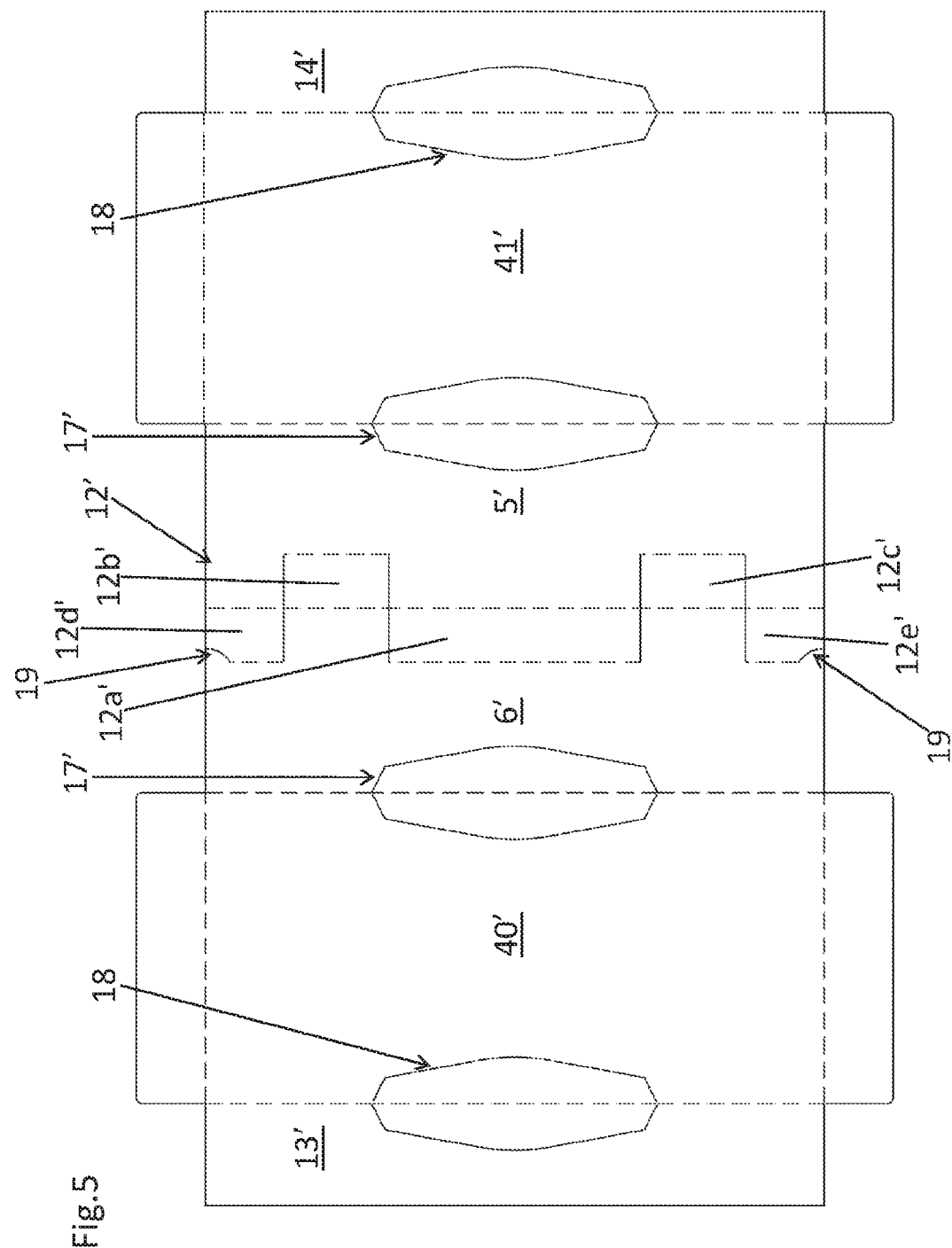
FIG. 5 is a view of the blank for obtaining the sleeve, the guide flaps and the connection element of the package of FIG. 1.

With reference to the attached figures, a package for components of aerosol generating devices object of the present invention has been generically denoted with the reference numeral 1.

An aerosol generating device generally comprises a battery, an atomizer which is powered by the battery and a cartridge containing an aromatised liquid or, possibly, a powdered material.

By the term "Component" we mean a part of an aerosol generating device. In particular, the component can be a cartridge comprising: a tubular containment body (preferably cylindrical); a vaporisable material contained in the tubular body; a cap that closes the tubular body to prevent the spilling of the vaporizable material.

With reference to FIGS. 1-7, a first embodiment of a package according to the present invention is described in the following.

The package 1 comprises: four components (not illustrated, which can be cartridges, for example); a first blister pack 2 comprising two housings 20 containing two of the components; a second blister pack 3 comprising two housings 30 containing the further two components; a sleeve 4 comprising a first wall 40 and a second wall 41 opposite and parallel to each other, and a first opening 42 and a second opening 43 opposite to each other.

The first blister pack 2 and the second blister pack 3 are slidable relative to the sleeve 4, respectively through the first opening 42 and the second opening 43, between an extraction position A (FIGS. 2, 3 and 2A, 3A) in which it is possible to extract the components and a closing position B (FIGS. 1 and 1A) in which the access to the components is prevented.

The package 1 further comprises: a first guide flap 5 which extends from the second wall 41 of the sleeve 4, between the first wall 40 and the second wall 41 at the second opening 43, to form a first slot 50 with the second wall 41; a second guide flap 6 which extends from the first wall 40 of the sleeve 4, between the first wall 40 and the second wall 41 at the first opening 42, to create a second slot 60 with the first wall 40.

Moreover, the package 1 comprises a first sliding flap 7 integral with the first blister pack 2 and a second sliding flap 8 integral with the second blister pack 3 which are arranged in the first slot 50 and in the second slot 60, respectively, and are shaped to slide in the first slot 50 and in the second slot 60, respectively.

Therefore, due to the configuration and arrangement of the first guide flap 5, of the second guide flap 6, of the first sliding flap 7 and of the second sliding flap 8, the proposed package 1 allows the sliding of the first blister pack 2 and of the second blister pack 3 relative to the sleeve 4. Accordingly, simply by extracting the first blister pack 2 and/or the second blister pack 3 from the sleeve 4 the smoker can have access the components. Moreover, the fact of comprising a pair of blister packs 2, 3 and a single sleeve 4 (there is no sleeve for each blister pack), allows the proposed package 1 to optimize the number of components it can contain in relation to the quantity of material used for obtaining the package 1.

With reference to FIG. 1, in addition to the first wall 40 and to the second wall 41, the sleeve 4 comprises: a third wall 44 which connects the first wall 40 and the second wall 41; a fourth wall 45 which connects the first wall 40 and the second wall 41 and which is opposite and parallel to the third wall 44.

The first blister pack 2 and the second blister pack 3 can be made by means of a portion of plastic material which defines the housings 20, 30 for the components and an aluminium sheet which is fixed (in particular, heat-welded) to the portion of plastic material to close the housings 20, 30.

With reference to FIG. 7, the first blister pack 2 of the package of FIG. 1 is illustrated. It is understood that the second blister pack 3 preferably has the same shape, sizes and materials as the first blister pack 2. In said illustrated embodiment, the first blister pack 2 (and similarly also the second blister pack 3) has a rectangular shape, a longitudinal development axis Y, and comprises a pair of housings 20 each containing a component for an aerosol generating device. It is understood that the first blister pack 2 and the second blister pack 3 can have a different shape and size from the one illustrated in FIG. 7; for example, the first blister pack 2 and the second blister pack 3 can comprise a single housing 20, 30 or more than two housings 20, 30.

Preferably, the package 1 comprises a first support element 9 and a second support element 10 carrying the first blister pack 2 and the second blister pack 3, respectively.

With particular reference to FIGS. 4 and 4A, the first support element 9 and the second support element 10 each comprise a first portion 9a, 10a comprising a pair of windows 11 sized to each receive a housing 20, 30 of the first blister pack 2 and of the second blister pack 3, respectively, and a second portion 9b, 10b which is opposite to the first portion 9a, 10a and that is fixed to the first portion 9a, 10a to hold the first blister pack 2 and the second blister pack 3.

Moreover, the first sliding flap 7 and the second sliding flap 8 are fixed (preferably, are as a single body) to the first support element 9 and to the second support element 10, respectively.

Advantageously, the first support element 9 and the second support element 10 provide a greater structure to the package in addition to a pleasant aesthetic impact. Moreover, the first support element 9 and the second support element 10 can be made of cardboard. Advantageously, it is easy and inexpensive to customize the package 1 with printing at the first support element 9 and/or of the second support element 10.

With reference, for example, to FIG. 3, when both the first blister pack 2 and the second blister pack 3 are in the extraction position A, the first blister pack 2 shows the components to the smoker while at the second portion 10b of the second support element 10 information regarding the components contained in the housings 20 of the first blister pack 2 can be illustrated.

It is specified that the number of windows 11 of the first portion 9a of the first support element 9 is equal to the number of housings 20 of the first blister pack 2. Similarly, the number of windows 11 of the first portion 10a of the second support element 10 is equal to the number of housings 30 of the second blister pack 3.

With reference to FIG. 6, the blank 9' is illustrated, the first support element 9 of the package 1 of FIGS. 1-3 is obtained from the folding thereof (the blank for obtaining the second connection element 10 is the same); in said embodiment the first support element 9, the first sliding flap 7 and the second abutting flap 16 are made as a single body. Said blank 9' comprises: a first panel 9a' having the pair of windows 11 and having a C-shape, which first panel 9a' is designed to define the first portion 9a of the first support element 9 and a part of the first tab 70 and of the second tab 71 of the first sliding flap 7; a second panel 9b' that is articulated with the first panel 9a', which has a C-shape and that is designed to define the second portion 9b of the first support element and a further part of the first tab 70 and of the second tab 71 of the first sliding flap 7; an abutting panel 16' designed to define the second abutting flap 16. In particular, the first tab 70 and the second tab 71 are defined by the overlapping of the first panel 9a' and of the second panel 9b'.

According to an alternative embodiment, the second portion 9b of the first support element 9 and the second portion 10b of the second support element 10 each comprise at least one window 11' facing the window 11 of the respective first portion 9a, 10a (said embodiment is obtained starting from the blank of FIG. 10). Advantageously, the extraction of the components from the respective housing 20, 30 will prove to be particularly easy and fast.

It is understood that the number of windows 11' of the second portion 9b of the first support element 9 is equal to the number of windows 11 of the first portion 9a of the first support element 9. Similarly, the number of windows of the second portion 10b of the second element support 10 is equal to the number of windows 11 of the second portion 11a of the second support element 10.

In a further alternative embodiment, the second portion 9b of the first support element 9 and the second portion 10b of the second support element 10 each comprise at least one weakening line 110 that defines a part of the second portion 9b, 10b which faces the window 11 of the respective first portion 9a, 10a (said embodiment is obtained starting from the blank of FIG. 11). Advantageously, the extraction of the components requires the removal of the part of second portion 9*b*, 10*b* defined by the weakening line 110 and this will prove to be particularly easy and fast thanks to the weakening line 110.

It should be noted that by the term "weakening line" we mean a line made up of incisions alternating with joining points (known as nicks) or a continuous line incised for half the thickness of the blank is to be intended.

The first sliding flap 7 and the second sliding flap 8 can each comprise a first tab 70, 80 and a second tab 71.

The first blister pack 2 and the second blister pack 3, as said, have a longitudinal development axis Y. The first tab 70 and the second tab 71 of the first sliding flap 7 are integral with the first blister pack 2 in proximity of opposite ends of the first blister pack. 2. The first tab 80 and the second tab of the second sliding flap 8 are integral with the second blister pack 3 in the vicinity of opposite ends of the second blister pack 3.

Said configuration of the first sliding flap 7 and of the second sliding flap 8 and said reciprocal arrangement thereof with the first blister pack 2 and with the second blister pack 3 allow, when the first blister pack 2 and the second blister pack 3 are in the closing configuration B (FIGS. 1 and 1A) to have a central area of the package 1 in which there are neither the blister packs 2, 3 nor any sliding flap 7, 8. Therefore, the smoker holding the package 1 in hand, in order to extract the first blister pack 2 and/or the second blister pack 3, will grasp the package 1 at the centre without impeding the sliding of the first blister pack 2 and/or of the second blister pack 3 relative to the sleeve 4.

In detail, with particular reference to FIGS. 4 and 4A, the first tab 70 and the second tab 71 of the first sliding flap 7 are fixed (or preferably made as a single body) to the first support element 9 and the first tab 80 and second tab of the second sliding flap 8 are fixed (or preferably made as a single body) to the second support element 10.

In other words, the first support element 9, formed by the overlapping of the first portion 9*a* and of the second portion 9*b*, has a longitudinal development which is orthogonal to the sliding direction X and parallel to the longitudinal development axis Y of the first blister pack 2; the first tab 70 and the second tab 71 of the first sliding tab 7 are fixed at opposite ends of the first support element 9. With further detail, said first tab 70 and second tab 71 have a development orthogonal to the development of the first support element 9. In other words, the first support element 9, the first tab 70 and the second tab 71 are mutually arranged with a C-shape (FIG. 4).

Similarly, the second support element 10, formed by the overlapping of the first portion 10*a* and of the second portion 10*b*, has a longitudinal development which is orthogonal to the sliding direction X and parallel to the longitudinal development axis Y of the second blister pack 3; the first tab 80 and the second tab of the second sliding flap 8 are fixed at opposite ends of the second support element 10. With further detail, said first tab 80 and second tab have a development orthogonal to the development of the second support element 10. In other words, the second support element 10, the first tab 80 and the second tab are mutually arranged with a C-shape.

Preferably, the first support element 9 and the second support element 10 have the same in shape, sizes and material.

Preferably, the package 1 comprises a connection element 12 that is arranged between the first wall 40 and the second wall 41 of the sleeve 4 and which comprises a first connection wall connecting the first guide flap 5 and the second guide flap 6 to each other and which is transversal in respect to the sliding direction X. In detail, the first connection wall is fixed (or preferably made as a single body) to the first guide flap 5 and to the second guide flap 6.

The connection element 12 therefore prevents the package 1 from inflating centrally. Advantageously, the connection element 12 confers greater stability to the package 1. In other words, the connection element 12 proves to be the load-bearing structure of the package 1.

The connection element 12 is preferably a hollow tubular element arranged orthogonal to the sliding direction X.

Preferably, the first connection wall is arranged between the first tab 70 and the second tab 71 of the first sliding flap 7 and between the first tab 80 and the second tab of the second sliding flap 8.

In other words, the first connection wall has a development orthogonal to the sliding direction X and has a length, in said development direction, which is smaller than the distance between the third wall 44 and the fourth wall 45 of the sleeve 4. In detail, the first tab 70, 80 of the first sliding flap 7 and of the second sliding flap 8 are arranged between one end of the first connection wall and the third wall 44, while the second tab 71 of the first sliding flap 7 and of the second sliding flap 8 are arranged between the other end of the first connection wall and the fourth wall 45.

Preferably, the connection element 12 comprises a second connection wall 12*b* that is parallel to the first connection wall, which connects the first guide flap 5 and the second guide flap 6 and that is spaced, along the sliding direction X, from the first connection wall.

Advantageously, the first connection wall and the second connection wall 12*b* create a hollow tubular area in the centre of the package 1.

Preferably, the first and second connection walls 12*b* are not facing each other. In other words, the first wall and the second connection wall 12*b* are staggered along an axis of the package 1 orthogonal to the sliding direction X.

Moreover, the connection element 12 comprises a third connection wall that is parallel to the first connection wall, which connects the first guide flap 5 and the second guide flap 6 and that is spaced, along the sliding direction X, from the first connection wall. The first connection wall is arranged between the second connection wall 12*b* and the third connection wall.

Preferably, the first and second connection walls 12*b* are not facing each other. Similarly, also the first connection wall and the third connection wall are not facing each other.

The connection element 12 also comprises a fourth connection wall 12*d* and a fifth connection wall that are parallel to the first connection wall, which connect the first guide flap 5 and the second guide flap 6 and that are aligned, along the sliding direction X, with the first connection wall (they are spaced, along the sliding direction X from the second connection wall 12*b* and from the third connection wall). The fourth connection wall 12*d* is arranged between the second connection wall 12*b* and the third wall 44; the fifth connection wall is arranged between the third connection wall and the fourth wall 45.

Preferably, the second and fourth connection walls 12*b*, 12*d* are not facing each other. Similarly, also the third connection wall and the fifth connection wall are not mutually faced.

The package 1 has an axis of symmetry Z which is orthogonal to the sliding direction X. The first blister pack 2 is arranged, relative to the second blister pack 3, rotated by 180° about said axis of symmetry Z. Advantageously, said mutual arrangement of the first blister pack 2 and of the second blister pack 3, allows to obtain a more compact package 1.

The first guide flap 5 can be partially fixed to the first wall 40 of the sleeve 4 and the second guide flap 6 can be partially fixed (for example, by glue or adhesive) to the second wall 41 of the sleeve 4.

In detail, the first guide flap 5 and the second guide flap 6 are fixed to the first wall 40 and to the second wall 41, respectively, at a respective central portion. Accordingly, the first slot 50 and the second slot 60 are each formed by two parts and the fixed central portion of the first guide flap 5 and of the second guide flap 6 is interposed between said two parts of the first slot 50 and of the second slot 60.

Moreover, the package 1 comprises stopping means for limiting the sliding of the first blister pack 2 and of the second blister pack 3 relative to the sleeve 4.

In detail, preferably the package 1 comprises: a first stop flap 13 that is fixed to the first wall 40 of the sleeve 4, between the first wall 40 and the second wall 41, at the second opening 43; a second stop flap 14 that is fixed to the second wall 41 of the sleeve 4, between the first wall 40 and the second wall 41, at the first opening 42; a first stop flap 15 that is arranged between the second sliding flap 8 and the first wall 40 to abut the first stop flap 13 when the second blister pack 3 is in the extraction position A; a second abutting flap 16 that is arranged between the first sliding flap 7 and the second wall 41 to abut the second stop flap 14 when the first blister pack 2 is in the extraction position A.

Advantageously, the first blister pack 2 and the second blister pack 3 cannot be completely extracted from the sleeve 4.

With reference to the package 1 of FIGS. 1 to 7, the first abutting flap 15 comprises two parts, one at the first tab 80 and one at the second tab of the second sliding flap 8. Similarly, the second abutting flap 16 comprises two parts, one at the first tab 70 and one at the second tab 71 of the first sliding flap 7.

The sleeve 4, the first and second guide flap 5, 6, the first and second stop flap 13, 14 and the connection element 12 are made as a single body (preferably, in cardboard). In particular, they are made starting from the same blank illustrated in FIG. 5. In FIG. 5 the various parts of the blank have been marked, where possible, with accented reference numbers equal to the reference numbers which distinguish the corresponding parts of the sleeve 4, the first and second guide flaps 5, 6, of the first and second stop flap 13, 14 and of the connection element 12.

With reference to FIG. 5, the blank comprises a connection panel 12' designed to define the connection element 12 that is articulated on one side to a first guide panel 5', which is designed to define the first guide flap 5 (and on the other side to a second guide panel 6', which is designed to define the second guide flap 6).

In detail, the connection panel 12' comprises a first part 12a' designed to define the first connection wall, a second part 12b' designed to define the second connection wall 12b, a third part 12c' designed to define the third connection wall, a fourth part 12d' designed to define the fourth connection wall 12d and a fifth part 12e' designed to define the fifth connection wall.

The first guide flap 5 comprises at respective ends a pair of appendages 19. Said appendages 19 extend the size of the first slot 50 along the sliding direction X. In this way, even when the first blister pack 2 is in the extraction position A, the first sliding flap 7 is arranged in the first slot 50. Said appendages 19 are made by an incision at the fourth part 12d' and at the fifth part 12e' of the connection panel 12' (FIG. 5).

Said appendages 19 are not necessary at the second guide flap 6 because the length of the second slot 60 along the sliding direction X is greater than the length of the first slot 50. The first part 12a' is arranged centrally with respect to the second part 12b' and to the third part 12c' and is separated from them by means of respective incision lines. Similarly, the fourth part 12d' is separated from the second part 12b' by an incision line and the fifth part 12e' is separated from the fourth part 12c' by a further incision line.

With reference to the blank of FIG. 5, pre-fold or weakening lines have been denoted with dotted lines while cut or incision lines have been denoted with continuous lines (said division has been used also with reference to the blanks of FIGS. 6, 9A, 9B, 10 and 11).

Figure 9B:
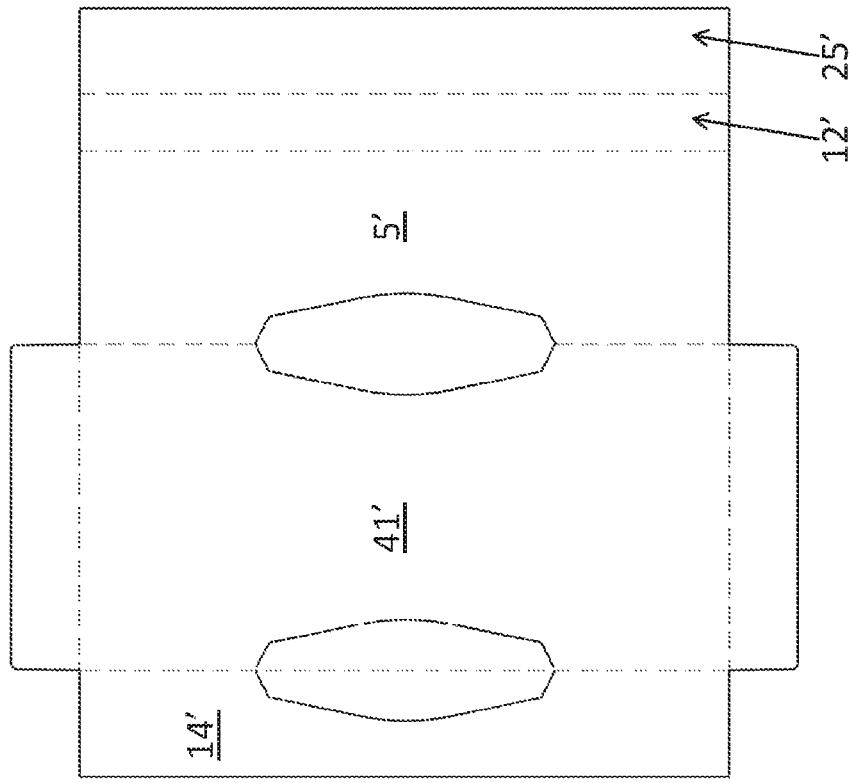
FIGS. 9A and 9B are views of blanks which, when connected, obtain the sleeve, the guide flaps and the connection element of the package of FIG. 8.
Figure 9A:
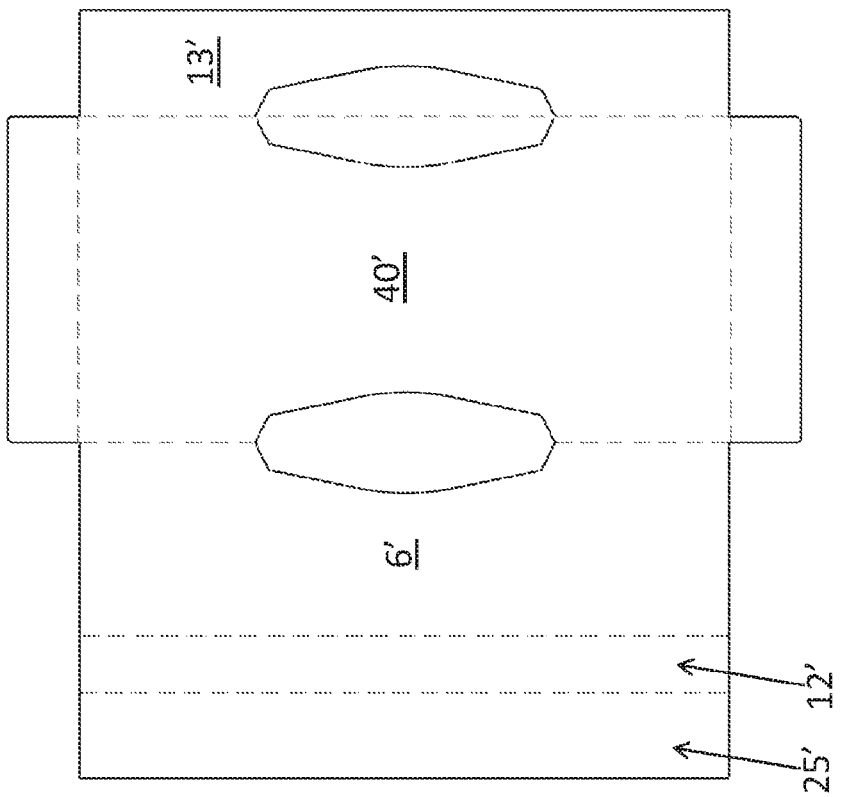

Alternatively, according to the embodiment of the package 1 illustrated in FIG. 8, the sleeve 4, the first guide flap 5, the second guide flap 6 and the connection element 12 could be made starting from two distinct blanks (see FIGS. 9A and 9B, in which the various parts have been marked, where possible, with accented reference numbers which distinguish the corresponding parts of the sleeve 4, of the first and second guide flap 5, 6, of the first and second stop flap 13, 14 and of the connection element 12).

With reference to FIG. 9A, a first blank is illustrated, from the folding thereof the first wall 40 of the sleeve 4, the second guide flap 6 and part of the connection element 12 are obtained, Similarly, with reference to FIG. 9B, a second blank (having the same shape and dimensions as the first blank) is illustrated, from the folding thereof the second wall 41 of the sleeve 4, the first guide flap 5 and part of the connection element 12 are obtained. The two blanks, before or after or during folding, are connected together by means glue by using the connection panels 25'.

With reference to FIGS. 1-3, the package 1 comprises a recess 17 formed in the first wall 40 of the sleeve 4 at the first opening 42 and a further recess formed in the second wall 41 of the sleeve 4 at the second opening 43. Advantageously, said recesses 17 make the extraction of the first blister pack 2 and of the second blister pack 3 from the sleeve 4 easier.

Furthermore, the package 1 may comprise a partial incision line 18 in the first wall 40 of the sleeve 4 at the second opening 43 and a partial incision line in the second wall 41 of the sleeve 4 at the first opening 42. The incision lines define a part 40a of first wall 40 and a part of second wall which, before the first extraction of the first blister pack 2 and of the second blister pack 3, are fixed to the first wall 40 and to the second wall 41, respectively, at at least one point. Said parts 40a are respectively connected to the second blister pack 3 (for example, glued to the second support element 10) and to the first blister pack 2 (for example, glued to the first support element 9) and, at the first extraction of the first and second blister packs 2 3 from the sleeve 4, said parts 40a are detached from the first wall 40 and from the second wall 41 and remain connected to the second blister pack 3 and to the first blister pack 2. Advantageously, it is easier to extract the second blister pack 3 while, at the same time, maintaining a pleasant aesthetic appearance of the package 1.

According to a further embodiment not illustrated, the package 1 may be privy of the first support element 9 and the second support element 10. In this case, the first sliding flap 7 and the second sliding flap 8 are fixed to the first blister pack 2 and to the second blister pack 3.

In this embodiment not illustrated, the first sliding flap 7 and the second sliding flap 8 can be as a single body with the first blister pack 2 and with the second blister pack 3. In this case, too, the first sliding flap 7 and the second sliding flap 8 can each comprise a first tab and a second tab.

The first blister pack 2 has a longitudinal development and the first tab and the second tab of the first sliding flap are fixed (or better, made as a single body) at opposite ends of the first blister pack 2. Similarly, the second blister pack 3 has a longitudinal development and the first tab and the second tab of the second sliding flap 8 are fixed at opposite ends of the second blister pack 3.

In the latter embodiment, the first blister pack 2 and the second blister pack 3 have a C-shape.

The invention claimed is:

1. A package (1) for components of aerosol generating devices; the package (1) comprises:
    at least two components;
    a first blister pack (2) comprising a first housing (20) containing a first component;
    a second blister pack (3) comprising a second housing (30) containing a second component; and
    a sleeve (4) comprising a first wall (40) and a second wall (41) opposite and parallel to each other, and a first opening (42) and a second opening (43) opposite to each other;
    wherein the first blister pack (2) and the second blister pack (3) are slidable along a sliding direction (X) and relative to the sleeve (4), respectively through the first opening (42) and the second opening (43), between an extraction position (A) in which it is possible to extract the component and a closing position (B) in which the access to the component is prevented;
    wherein a first guide flap (5) is provided, which develops from the second wall (41) of the sleeve (4), between the first wall (40) and the second wall (41) at the second opening (43), to form a first slot (50) with the second wall (41);
    wherein a second guide flap (6) is provided, which develops from the first wall (40) of the sleeve (4), between the first wall (40) and the second wall (41) at the first opening (42), to form a second slot (60) with the first wall (40);
    wherein a first sliding flap (7) is provided, which is integral with the first blister pack (2), is arranged in the first slot (50), and is shaped to slide in the first slot (50);
    wherein a second sliding flap (8) is provided, which is integral with the second blister pack (3), is arranged in the second slot (60), and is shaped to slide in the second slot (60); and
    wherein a connection element (12) is provided, which is arranged between the first wall (40) and the second wall (41) of the sleeve (4) and which comprises a first connection wall which connects the first guide flap (5) and the second guide flap (6) to each other and which is transverse to the sliding direction (X);
        wherein a first support element (9) and a second support element (10) are provided, which respectively carry the first blister pack (2) and the second blister pack (3);
        wherein the first support element (9) and the second support element (10) comprise each a first portion (9a, 10a), comprising a window (11) sized to receive the housing (20, 30) of the first blister pack (2) and of the second blister pack (3), respectively, and a second portion (9b, 10b) which is opposite to the first portion (9a, 10a) and fixed to the first portion (9a, 10a) to enclose the first blister pack (2) and the second blister pack (3);
        wherein the first sliding flap (7) and the second sliding flap (8) are respectively fixed to the first support element (9) and to the second support element (10);
        wherein the second portion (9b) of the first support element (9) and the second portion (10b) of the second support element (10) each comprise a window (11') faced to the window (11) of the respective first portion (9a, 10a);
        wherein the first sliding flap (7) and the second sliding flap (8) each comprise a first tab (70, 80) and a second tab (71);
        wherein the first blister pack (2) has a longitudinal development axis (Y) and the first tab (70) and the second tab (71) of the first sliding flap (7) are integral with the first blister pack (2) in proximity of the opposite ends of the first blister pack (2); and
    wherein the second blister pack (3) has a longitudinal development axis (Y) and the first tab (80) and the second tab of the second sliding flap (8) are integral with the second blister pack (3) in proximity of the opposite ends of the second blister pack (3).

2. The package according to claim 1, wherein the first sliding flap (7) and the second sliding flap (8) are made in a single body with the first blister pack (2) and the second blister pack (3), respectively.

3. The package (1) according to claim 1, wherein:
    the first support element (9) and the first tab (70) and the second tab (71) of the first sliding flap (7) are made in a single body and arranged to form a C-shape;
    the second support element (10) and the first tab (80) and the second tab of the second sliding flap (8) are made in a single body and arranged to form a C-shape.

4. The package according to claim 1, wherein the first connection wall is arranged between the first tab (70) and the second tab (71) of the first sliding flap (7) and between the first tab (80) and the second tab (80) of the second sliding flap (8).

5. The package (1) according to claim 1, wherein the connection element (12) comprises at least a second connection wall (12b) parallel to the first connection wall, connecting the first guide flap (5) and the second guide flap (6) and which is spaced, along the sliding direction (X), from the first connection wall.

6. The package (1) according to claim 1, having an axis of symmetry (Z) orthogonal to the sliding direction (X) and wherein the first blister pack (2) is arranged, with respect to the second blister pack (3), rotated by 180° around said axis of symmetry (Z).

7. The package (1) according to claim 1, wherein the first guide flap (5) is partially fixed to the first wall (40) of the sleeve (4) and the second guide flap (6) is partially fixed to the second wall (41) of the sleeve (4).

8. The package (1) according to claim 1 and comprising:
    a first stop flap (13) fixed to the first wall (40) of the sleeve (4), between the first wall (40) and the second wall (41), at the second opening (43);
    a second stop flap (14) which is fixed to the second wall (41) of the sleeve (4), between the first wall (40) and the second wall (41), at the first opening (42);
    a first abutting flap (15) arranged between the second sliding flap (8) and the first wall (40) to abut the first stop flap (13) when the second blister pack (3) is in the extraction position (A); and
    a second abutting flap (16) arranged between the first sliding flap (7) and the second wall (41) to abut the second stop flap (14) when the first blister pack (2) is in the extraction position (A).

9. The package (1) according to claim 1, wherein:
the first guide flap (5) is arranged inside the sleeve (4), has a more limited extension with respect to the second wall (41) of the sleeve (4), is arranged parallel to, and at a given distance from the second wall (41) of the sleeve (4), extends from the second wall (41) of the sleeve (4) by means of a "U" shaped fold arranged at the second opening (43), terminates before a centerline of the sleeve (4), and forms a first slot (50) with the second wall (41); and
the second guide flap (6) is arranged inside the sleeve (4), has a more limited extension with respect to the first wall (40) of the sleeve (4), is arranged parallel to, and at a given distance from the first wall (40) of the sleeve (4), extends from the first wall (40) of the sleeve (4) by means of a "U" shaped fold arranged at the first opening (42), terminates before the centerline of the sleeve (4), and creates a second slot (60) with the first wall (40).

10. A package (1) for components of aerosol generating devices; the package (1) comprises:
at least two components;
a first blister pack (2) comprising a first housing (20) containing a first component;
a second blister pack (3) comprising a second housing (30) containing a second component;
a sleeve (4) comprising a first wall (40) and a second wall (41) opposite and parallel to each other, and a first opening (42) and a second opening (43) opposite to each other;
a first stop flap (13) fixed to the first wall (40) of the sleeve (4), between the first wall (40) and the second wall (41), at the second opening (43);
a second stop flap (14) fixed to the second wall (41) of the sleeve (4), between the first wall (40) and the second wall (41), at the first opening (42);
a first abutting flap (15) arranged between the second sliding flap (8) and the first wall (40) to abut the first stop flap (13) when the second blister pack (3) is in the extraction position (A); and
a second abutting flap (16) arranged between the first sliding flap (7) and the second wall (41) to abut the second stop flap (14) when the first blister pack (2) is in the extraction position (A);
wherein the first blister pack (2) and the second blister pack (3) are slidable along a sliding direction (X) and relative to the sleeve (4), respectively through the first opening (42) and the second opening (43), between an extraction position (A) in which it is possible to extract the component and a closing position (B) in which the access to the component is prevented;
wherein a first guide flap (5) is provided, which develops from the second wall (41) of the sleeve (4), between the first wall (40) and the second wall (41) at the second opening (43), to form a first slot (50) with the second wall (41);
wherein a second guide flap (6) is provided, which develops from the first wall (40) of the sleeve (4), between the first wall (40) and the second wall (41) at the first opening (42), to form a second slot (60) with the first wall (40);
wherein a first sliding flap (7) is provided, which is integral with the first blister pack (2), is arranged in the first slot (50), and is shaped to slide in the first slot (50);
wherein a second sliding flap (8) is provided, which is integral with the second blister pack (3), is arranged in the second slot (60), and is shaped to slide in the second slot (60); and
wherein a connection element (12) is provided which is arranged between the first wall (40) and the second wall (41) of the sleeve (4) and which comprises a first connection wall which connects the first guide flap (5) and the second guide flap (6) to each other and which is transverse to the sliding direction (X).

11. A package (1) for components of aerosol generating devices; the package (1) comprises:
at least two components;
a first blister pack (2) comprising a first housing (20) containing a first component;
a second blister pack (3) comprising a second housing (30) containing a second component; and
a sleeve (4) comprising a first wall (40) and a second wall (41) opposite and parallel to each other, and a first opening (42) and a second opening (43) opposite to each other;
wherein the first blister pack (2) and the second blister pack (3) are slidable along a sliding direction (X) and relative to the sleeve (4), respectively through the first opening (42) and the second opening (43), between an extraction position (A) in which it is possible to extract the component and a closing position (B) in which the access to the component is prevented;
wherein a first guide flap (5) is provided, which develops from the second wall (41) of the sleeve (4), between the first wall (40) and the second wall (41) at the second opening (43), to form a first slot (50) with the second wall (41);
wherein a second guide flap (6) is provided, which develops from the first wall (40) of the sleeve (4), between the first wall (40) and the second wall (41) at the first opening (42), to form a second slot (60) with the first wall (40);
wherein a first sliding flap (7) is provided, which is integral with the first blister pack (2), is arranged in the first slot (50), and is shaped to slide in the first slot (50);
wherein a second sliding flap (8) is provided, which is integral with the second blister pack (3), is arranged in the second slot (60), and is shaped to slide in the second slot (60);
wherein a connection element (12) is provided which is arranged between the first wall (40) and the second wall (41) of the sleeve (4) and which comprises a first connection wall which connects the first guide flap (5) and the second guide flap (6) to each other and which is transverse to the sliding direction (X);
wherein the first guide flap (5) is arranged inside the sleeve (4), has a more limited extension with respect to the second wall (41) of the sleeve (4), is arranged parallel to, and at a given distance from the second wall (41) of the sleeve (4), extends from the second wall (41) of the sleeve (4) by means of a "U" shaped fold arranged at the second opening (43), terminates before a centerline of the sleeve (4), and forms a first slot (50) with the second wall (41); and
wherein the second guide flap (6) is arranged inside the sleeve (4), has a more limited extension with respect to the first wall (40) of the sleeve (4), is arranged parallel to, and at a given distance from the first wall (40) of the sleeve (4), extends from the first wall (40) of the sleeve (4) by means of a "U" shaped fold arranged at the first opening (42), terminates before the centerline of the sleeve (4), and creates a second slot (60) with the first wall (40).

\* \* \* \* \*